United States Patent
Peres et al.

(10) Patent No.: US 11,065,094 B2
(45) Date of Patent: Jul. 20, 2021

(54) BIOLOGICAL PROSTHESIS INTENDED FOR THE TREATMENT OF PARASTOMAL HERNIAS

(71) Applicant: MECCELLIS BIOTECH, La Rochelle (FR)

(72) Inventors: Anthony Peres, Dompierre sur Mer (FR); Guillaume Hofmanski, Mieuxce (FR); Aurelie Lammelin, Richebourg (FR)

(73) Assignee: MECCELLIS BIOTECH, La Rochelle (FR)

( * ) Notice: Subject to any disclaimer, the term of this patent is extended or adjusted under 35 U.S.C. 154(b) by 214 days.

(21) Appl. No.: 16/310,611

(22) PCT Filed: Jun. 16, 2017

(86) PCT No.: PCT/EP2017/064793
§ 371 (c)(1),
(2) Date: Dec. 17, 2018

(87) PCT Pub. No.: WO2017/216357
PCT Pub. Date: Dec. 21, 2017

(65) Prior Publication Data
US 2019/0209281 A1    Jul. 11, 2019

(30) Foreign Application Priority Data
Jun. 17, 2016   (FR) ........................ 1655645

(51) Int. Cl.
*A61F 2/00* (2006.01)
*A61L 27/36* (2006.01)

(52) U.S. Cl.
CPC .......... *A61F 2/0063* (2013.01); *A61L 27/362* (2013.01); *A61F 2250/0036* (2013.01)

(58) Field of Classification Search
CPC .......... A61F 2/0063; A61F 2/04; A61F 2/105; A61F 2230/0069; A61F 2230/0067; A61L 27/362; A61L 27/3604; A61L 27/3683; A61L 27/3691
See application file for complete search history.

(56) References Cited

U.S. PATENT DOCUMENTS

| 10,076,543 B2 * | 9/2018 | Wilhelmi ............ A61L 27/362 |
| 2013/0209572 A1 | 8/2013 | Wilhelmi et al. |
| 2016/0030487 A1 | 2/2016 | Bachrach et al. |

* cited by examiner

*Primary Examiner* — Brian A Dukert
*Assistant Examiner* — Amanda M Barkan
(74) *Attorney, Agent, or Firm* — Greer, Burns & Crain, Ltd.

(57) ABSTRACT

The subject of the invention is a biological prosthesis suitable for gastrointestinal surgery and in particular for the treatment of parastomal hernias. It has a thickness (12) of between 0.5 and 4 mm, consisting of dermis removed from a part of an animal belonging to the family of pigs, cattle or goats, with the said part of the animal corresponding to a part extending from the area (16) located at the base of the tail next to the junction of the last sacral vertebrae up to an area (18) starting at the base of the tail and encompassing the circumference of at least a part of the caudal vertebrae.

15 Claims, 1 Drawing Sheet

BIOLOGICAL PROSTHESIS INTENDED FOR THE TREATMENT OF PARASTOMAL HERNIAS

CROSS-REFERENCE TO RELATED APPLICATIONS

This application is a US national stage application of PCT/EP2017/064793 filed Jun. 16, 2017 which claims a benefit of priority to French Patent Application FR 1655645 filed Jun. 17, 2016, the entire disclosure of which is incorporated herein by reference.

TECHNICAL FIELD

This invention relates to a new biological prosthesis produced from an animal tail, which is particularly useful for the treatment of parastomal hernias.

BACKGROUND SECTION

A stoma is a small temporary or permanent opening created during a surgical operation to evacuate feces when they can no longer be evacuated through the natural passages. We know that between 50 and 70% of patients who have a permanent stoma suffer a parastomal hernia within the first three years. Patients must then undergo a new procedure to treat the hernia. However, such a procedure is complicated and the relapse rate is high. It is therefore necessary to implement a prosthetic device together with the surgery.

Currently, the prostheses used are synthetic prostheses. However, a synthetic prosthetic device is not recommended in this type of surgery because it causes discomfort to the patient, and pain. In addition, and most importantly, the use of a synthetic implant is not recommended for septic or potentially septic surgery, as is the case with parastomal surgery procedures. If an infection occurs, it is absolutely necessary to remove the prosthesis because it increases the risk of complications.

SUMMARY

The objective of the invention is to resolve these issues and to propose a biological prosthesis which is suitable for septic surgery, avoids pain, meets the requirements for the treatment of parastomal hernias, and is simple to produce and use.

For this purpose, this invention proposes to use dermis removed from a specific part of animals, located in the tail area.

Animal skin, in particular pig skin, has already been used for several years for the production of biological prostheses in various wall surgeries. Nevertheless, the use of animal dermis for the production of prostheses in cases of parastomal hernia would require many manipulations and assemblies of parts of dermis to obtain the desired shape, which seems hardly feasible from both a technical and economic point of view.

This invention concerns a biological prosthesis produced from a very specific part of the animal, which avoids these problems.

In effect, the invention concerns a biological prosthesis with a thickness of between 0.5 and 4 mm, consisting of dermis removed from a part of an animal belonging to the family of pigs, cattle or goats, with the said part of the animal corresponding to a part extending from the area located at the base of the tail next to the junction of the last sacral vertebrae up to an area starting at the base of the tail and encompassing the circumference of at least a part of the caudal vertebrae.

Advantageously, such a prosthesis has a shape which is highly suited to the treatment of parastomal hernias. It is simple to produce and, as a biological prosthesis, is suited to the surgical procedure to be carried out in septic or potentially septic conditions. Finally, it does not cause patients pain unlike existing prostheses for parastomal hernia.

Other characteristics and benefits will emerge from the detailed description of the invention which will follow, with regard to the appended figures.

DEFINITIONS

In the context of the invention, "acellularization" refers to the elimination of cellular elements. So that the prosthesis can be implanted in a recipient, the tissues removed from the donor animal are decellularized so as to decrease their immunogenicity. This processing involves the elimination of the donor animal's cells while maintaining the biological and mechanical properties of the extracellular matrix.

In the context of the invention, "deantigenization" refers to the elimination of proteins in the tissue from the donor animal that may not be recognized by the recipient of the prosthesis, causing the rejection of the implant. In effect, the donor animal may express enzymes or proteins in the tissue that are not expressed by the recipient. It is therefore important to eliminate these elements, in particular the epitope galactose-alpha-1,3-galactose (alpha-gal) which is found in the porcine species, in order to reduce the immune response after implantation in humans.

In the context of the invention, "truncated cone" refers to the general shape in the form of a cone which is open at its apex and which has edges, particularly towards the larger diameter, that may be festooned due to the general elasticity of the natural material. The truncated cone is located at the base of the tail; the base is open on the dorsal part of the animal resulting in a collar located perpendicular to the tail.

In the context of the invention, "cylindrical shape" refers to a general rotational form, not necessarily a perfectly cylindrical shape due to the natural material.

DETAILED DESCRIPTION OF THE INVENTION

Figure 1:
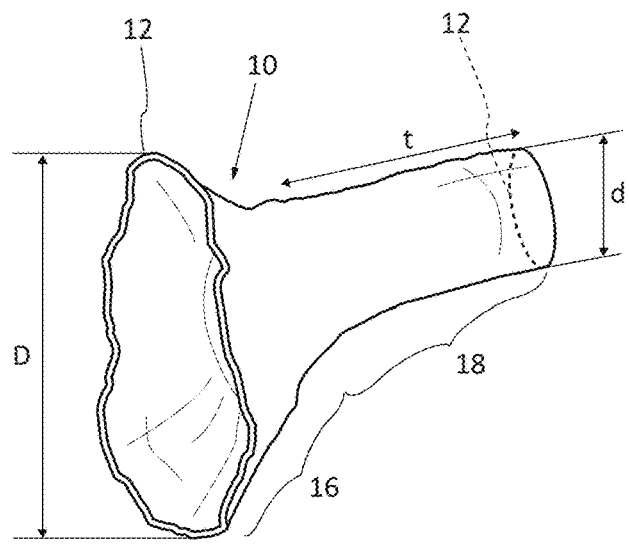
FIG. 1 presents a diagram of the prosthesis according to the invention.
Figure 2:
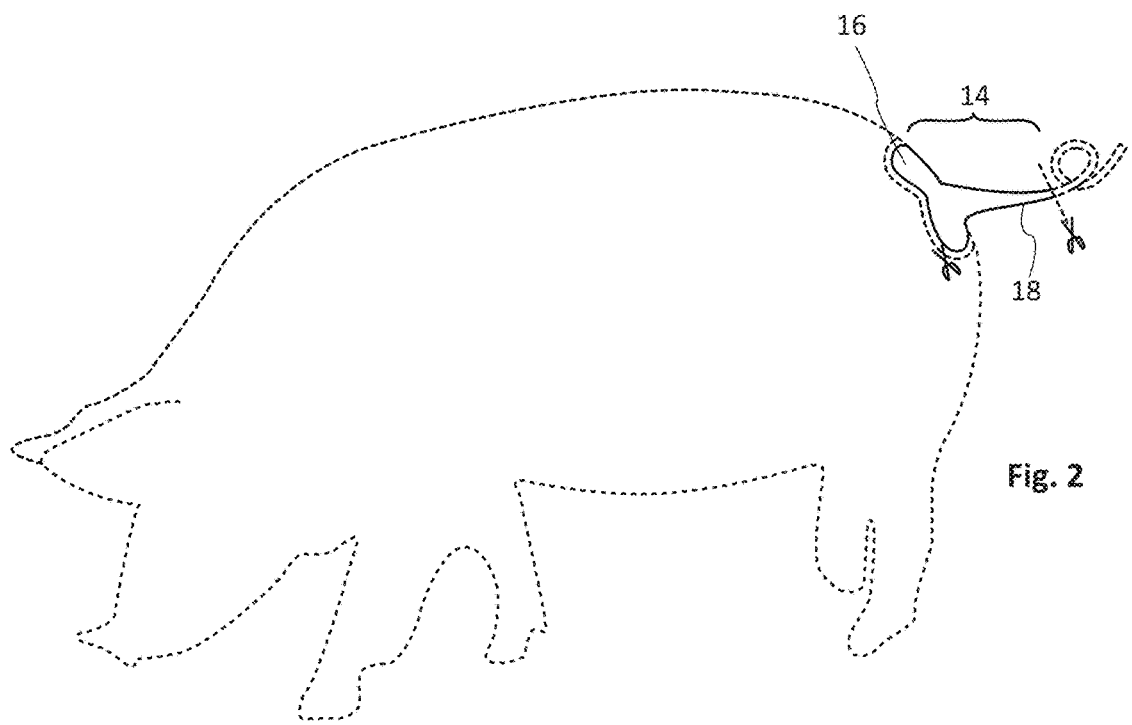
FIG. 2 presents a diagram of the removal of the part from the animal to produce the prosthesis according to the invention.
Figure 3:
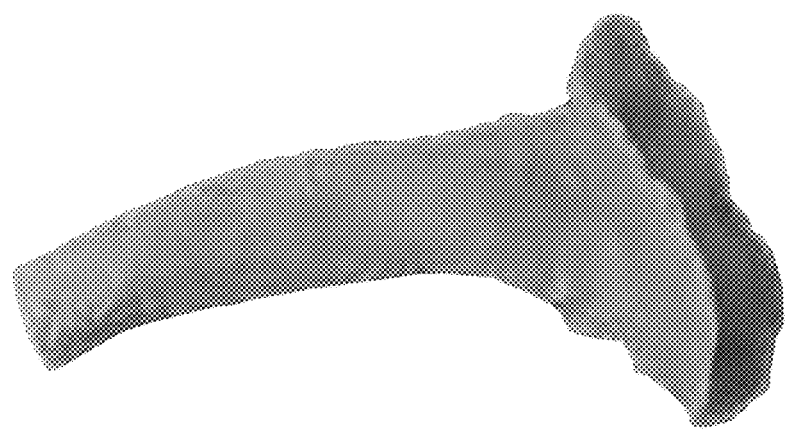
FIG. 3 presents a photograph of a prosthesis according to the invention.

According to a first aspect, the invention therefore concerns a biological prosthesis 10 such as presented in FIG. 1. It has a thickness 12 of between 0.5 and 4 mm, consisting of dermis removed from a part 14 of an animal belonging to the family of pigs, cattle or goats, with the said part 14 of the animal corresponding to a part extending from the area 16 located at the base of the tail next to the junction of the last sacral vertebrae up to an area 18 starting at the base of the tail and encompassing the circumference of at least a part of the caudal vertebrae.

The animal dermis, and in particular pig dermis, is particularly suited because its mechanical resistance allows it to be used in surgery. Furthermore, the composition of the extracellular matrix, in particular the collagen, of pig dermis is similar to that of human intestines.

To improve compatibility, the dermis is preferentially processed, in particular through acellularization and deantigenization. This processing makes it possible to eliminate in particular the cellular elements and the epitope alpha-gal which may cause an increased immune reaction and the acute rejection of the implant of animal origin.

Several methods known to the skilled person exist to process the dermis by acellularization and deantigenization, as for example those described in:

Badylak et al., "Extracellular Matrix as a Biological Scaffold Material: Structure and Function," *Acta Biomaterialia* (2008), doi:10.1016/j.actbio.2008.09.013

Xu et al., *Tissue Engineering*, Vol. 15, 143 (2009).

The thickness 12 of the dermis constituting the prosthesis is between 0.5 and 4 mm, preferentially between 0.5 and 2 mm. This thickness is necessary to ensure that the implant has good mechanical resistance. The thickness 12 varies depending on the desired mechanical resistance, because the greater the thickness, the less the material is flexible. To obtain such a thickness, it may be necessary to slice the dermis through its plane of thickness to the desired dimension, using sharp instruments such as a knife, for example. The mechanical resistance of the biological prosthesis 10 according the invention preferentially meets the following parameters (measured according to the methods described in Deeken et al. "Physicomechanical evaluation of absorbable and nonabsorbable barrier composite meshes for laparoscopic ventral hernia repair"):

A suture retention strength greater than 20 N,
A tear resistance greater than 20 N,
A ball burst strength greater than 50 N/cm.

According to a particularly suitable embodiment, the area 16 on the prosthesis, located at the base of the tail next to the junction of the last sacral vertebrae, is in the form of a truncated cone. Preferentially, the lower part of the truncated cone has a diameter D of between 2 and 8 cm, and even more preferentially between 4 and 7 cm.

The area 18 corresponds to all or part of the animal's tail. This area 18 is therefore has a cylindrical shape. The average diameter d of this area 18 is preferentially between 1 and 4 cm, and even more preferentially between 1.5 and 3 cm. This diameter is ideal for use in gastrointestinal surgery for the treatment of parastomal hernia. It can be adapted depending on the diameter of the stoma.

In addition, the size t of area 18 may correspond to the length of the tail or to a lesser length. Preferentially, this size t is between 1 and 8 cm, and preferentially between 1 and 4 cm.

The biological prosthesis 10 according to the invention may be dried to be stored. Preferentially, it is freeze-dried (lyophilized) because this drying technique is particularly suited to the preservation of collagen, which is a protein very sensitive to temperature. To be used, the prosthesis must be rehydrated by any known process for this purpose.

The biological prosthesis 10 according to the invention can be produced by any suitable process. Preferentially, it is produced by a production process comprising the following steps:

remove the integument of the animal from the part 14 in accordance with the desired dimensions,
separate the dermis from the rest of the integument,
potentially slice the dermis removed through its plane of thickness, to obtain the desired thickness 12,
processing of the dermis, in particular by acellularization and deantigenization,
sterilization.

Before removal, it is necessary to check that the animal's tail has a diameter d appropriate to the desired diameter for the prosthesis. This measurement can be taken by any means, for example using a caliper.

The removal is performed on a dead animal, just after it has been slaughtered, in the slaughterhouse itself.

The separation of the dermis from the rest of the integument is carried out using any cutting instrument, such as a knife, for example, preferentially immediately after the removal in the slaughterhouse.

The dermis is sliced using any cutting instrument, such as a knife, for example. This step must be performed with precision so as to obtain a uniform thickness over the whole of the implant.

Before or after sterilization, the process may include a freeze-drying (lyophilization) step. The biological prosthesis 10 according to the invention is preferentially packaged in sterile packaging.

Advantageously, the biological prosthesis retains the properties of the extracellular matrix from which it is extracted, and promotes the integration of tissue thus avoiding the erosion of adjacent tissues. In cases of post-operative sepsis and/or relapse, the prosthesis according to the invention must not be removed, unlike synthetic prostheses.

Its shape and its dimensions are perfectly suited to use in gastrointestinal surgery for the treatment of parastomal hernias.

The subject of the invention is therefore also a biological prosthesis 10 for use in gastrointestinal surgery, in particular in the treatment of parastomal hernias.

The prosthesis is used as existing synthetic prostheses, preferentially by implementing the following steps:

Circular incision of the skin in the area of the rectus abdominis muscle
Incision of the anterior aponeurosis of the rectus abdominis muscle
Circular, retromuscular dissection performed with the fingers
Incision of the posterior aponeurosis and peritoneum depending on the diameter (d) of the prosthesis,
Positioning and securing of the prosthesis (part 18) with separate stitches (6/8 sutures, slow resorption 2/0) on the posterior aponeurosis
Securing of the prosthesis (part 16) with separate stitches (4/6 sutures, slow resorption) on the anterior aponeurosis
Insertion of the loop of intestine into the prosthesis
Management of the stoma in the conventional manner.

The invention is now illustrated by a specific example of removal and production, and examples of biological prostheses according to the invention, produced according to this process.

Example Process

The tail of the animal is removed according to the claims after slaughter and before any other processing.

The dermis of the tail is then separated from the other anatomical elements of the tail using a knife in a manner that preserves as much of skin sheath as possible.

In order to obtain the desired thickness, the dermis can be sliced again using a knife or other cutting tools over the whole of the surface and in a uniform manner.

The prosthesis produced as a result is then processed by various chemical treatments so as to eliminate the cellular elements and other molecules that are specific to the donor organism.

The prosthesis is then freeze-dried for optimal storage but can also be stored by impregnating an appropriate chemical solution.

A final cutting procedure is performed in order to obtain the final desired dimensions. The implants are then sterilized using conventional techniques (EtO, gamma rays, Ebeam).

Examples of prostheses produced according to this process with a thickness of 1.5 mm:

Example 1 t=3 cm; d=2.5 cm; D=4.5 cm

Example 2 t=3 cm; d=3.5 cm; D=5 cm

Example 3 t=4 cm; d=4.5 cm; D=5 cm

The invention claimed is:

1. A biological prosthesis (10) consisting of a first portion (16) extending into a second portion (18), wherein the first portion is in a shape of a truncated cone and the second portion is in a cylindrical shape, wherein the biological prosthesis has a thickness (12) of between 0.5 and 4 mm, wherein the biological prosthesis consists of acellularized tail dermis removed from a part (14) of an animal belonging to a family of pigs, cattle or goats, with the said part (14) of the animal corresponding to a part extending from a first area (16) located at a base of a tail next to a junction of the last sacral vertebrae up to a second area (18) starting at the base of the tail and encompassing a circumference of at least a part of the caudal vertebrae.

2. The biological prosthesis according to claim 1, characterized in that the dermis is dermis processed by acellularization and antigenization.

3. The biological prosthesis (10) according to claim 1, characterized in that the first area (16) located at the base of the tail next to the junction of the last sacral vertebrae, is in a form of a truncated cone.

4. The biological prosthesis (10) according to claim 1, characterized in that the second area (18) encompassing the circumference of at least a part of the caudal vertebrae has a cylindrical shape.

5. The biological prosthesis (10) according to claim 1, characterized in that an average diameter of the second portion is between 1 and 4 cm.

6. The biological prosthesis (10) according to claim 1, characterized in that an average diameter (d) of the second portion (18) is between 1.5 and 3 cm.

7. The biological prosthesis (10) according to claim 1, characterized in that the thickness (12) is between 0.5 and 2 mm.

8. The biological prosthesis (10) according to claim 1, characterized in that a length (t) of the second portion (18) is between 1 and 8 cm.

9. The biological prosthesis (10) according to claim 1, characterized in that a length (t) of the second portion (18) is between 1 and 4 cm.

10. The biological prosthesis (10) according to claim 1, characterized in that a lower part of the truncated cone has a diameter D of between 2 and 8 cm.

11. The biological prosthesis (10) of claim 1, wherein the biological prosthesis is freeze-dried (lyophilized).

12. A production process of a biological prosthesis (10) according to claim 1, characterized in that it includes the following steps:
    removing an integument of an animal from the part (14) in accordance with desired dimensions wherein the removal is performed on a dead animal,
    separating dermis from the integument,
    processing the dermis by acellularization and antigenization, and
    sterilizing the biological prosthesis.

13. The production process according to claim 12, wherein the production process further includes, after processing, freeze-drying (lyophilizing) the dermis.

14. The production process of claim 12, wherein the production process further comprises slicing the dermis to obtain the dermis with a thickness between 0.5 and 4 mm.

15. The production process of claim 12, wherein the production process further includes packaging the sterilized biological prosthesis in sterile packaging.

* * * * *